(12) United States Patent
Ferlay et al.

(10) Patent No.: US 8,426,769 B2
(45) Date of Patent: Apr. 23, 2013

(54) METHOD AND DEVICE FOR DISPLAYING AND MONITORING THE PROFILE OF A WELD BEAD INSIDE A GROOVE PROVIDED BETWEEN TWO METAL WORKPIECES

(75) Inventors: Jean-Claude Ferlay, Chatenoy le Royal (FR); Jean-Mathieu Mestre-Bresson, Santenay (FR)

(73) Assignee: Areva NP, Courbevoie (FR)

( * ) Notice: Subject to any disclaimer, the term of this patent is extended or adjusted under 35 U.S.C. 154(b) by 1144 days.

(21) Appl. No.: 12/264,667

(22) Filed: Nov. 4, 2008

(65) Prior Publication Data
US 2009/0141965 A1 Jun. 4, 2009

(30) Foreign Application Priority Data
Nov. 6, 2007 (FR) ..................... 07 58813

(51) Int. Cl.
*B23K 26/03* (2006.01)
*B23K 31/02* (2006.01)

(52) U.S. Cl.
USPC .......... 219/121.83; 228/9; 228/103; 228/104; 228/105

(58) Field of Classification Search .......... None
See application file for complete search history.

(56) References Cited

U.S. PATENT DOCUMENTS

| | | | | |
|---|---|---|---|---|
| 4,827,099 A * | 5/1989 | Krebs et al. | ............. | 219/121.63 |
| 4,851,639 A * | 7/1989 | Sugitani et al. | ............. | 219/124.34 |
| 4,943,702 A * | 7/1990 | Richardson | ............. | 219/124.34 |
| 4,951,218 A * | 8/1990 | Okumura et al. | ............. | 700/212 |
| 4,965,499 A * | 10/1990 | Taft et al. | ............. | 318/568.11 |
| 4,988,201 A * | 1/1991 | Sugitani et al. | ............. | 356/601 |
| 5,045,668 A * | 9/1991 | Neiheisel et al. | ............. | 219/121.83 |
| 5,475,198 A * | 12/1995 | Burke et al. | ............. | 219/124.34 |
| 5,938,953 A * | 8/1999 | Jurca | ............. | 219/121.83 |
| 6,040,554 A * | 3/2000 | Terada et al. | ............. | 219/124.34 |
| 6,791,094 B1 * | 9/2004 | Olson et al. | ............. | 250/397 |
| 7,577,285 B2 * | 8/2009 | Schwarz et al. | ............. | 382/141 |
| 7,657,082 B2 * | 2/2010 | Kubo et al. | ............. | 382/154 |
| 2004/0011773 A1 * | 1/2004 | Fritz et al. | ............. | 219/121.83 |

(Continued)

FOREIGN PATENT DOCUMENTS

| | | | |
|---|---|---|---|
| EP | 358794 A | * | 3/1990 |
| JP | 02-104476 A | * | 4/1990 |
| JP | 03-005084 A | * | 1/1991 |
| JP | 06-246444 A | * | 9/1994 |

*Primary Examiner* — Kiley Stoner
(74) *Attorney, Agent, or Firm* — Novak Druce Connolly Bove + Quigg LLP

(57) ABSTRACT

The invention relates to a method of displaying and monitoring the profile of a weld bead (4), in which, placed inside the groove, there is an assembly (10) comprising, facing one another, an image acquisition means (11), a light source (12), the beam of which is directed towards said image acquisition means, and, between the image acquisition means and the light source, a mask (13); the optical axis of the image acquisition means (11) is oriented so as to be approximately parallel to the sidewalls (5, 6) of the groove (3); a light beam produced by the light source (12) is directed towards the mask (13) and the image acquisition means (11); a central shadow zone and a peripheral halo are formed by means of the light beam and the mask (13), said halo illuminating, approximately perpendicularly, the weld bead (4) and the sidewalls (5, 6); the profile of the weld bead (4) and the sidewalls (5, 6) are displayed on a display/monitoring means; and said assembly (10) is moved inside the groove (3) longitudinally and parallel to the sidewalls (5, 6).

19 Claims, 6 Drawing Sheets

U.S. PATENT DOCUMENTS

2005/0029326 A1* 2/2005 Henrikson ................ 228/8
2005/0103766 A1* 5/2005 Iizuka et al. ............ 219/124.34
2005/0224477 A1* 10/2005 McJunkin et al. ....... 219/124.34
2009/0128625 A1* 5/2009 Loipetsberger ................ 348/90

* cited by examiner

METHOD AND DEVICE FOR DISPLAYING AND MONITORING THE PROFILE OF A WELD BEAD INSIDE A GROOVE PROVIDED BETWEEN TWO METAL WORKPIECES

CROSS REFERENCE TO RELATED APPLICATIONS

This application claims priority under 35 U.S.C. §119(a) on Patent Application No. 0758813 filed in France on Nov. 6, 2007, the entire contents of which are hereby incorporated by reference.

The present invention relates to a method and to a device for displaying and monitoring the profile of a weld bead inside a groove provided between two metal workpieces.

In many industrial applications, metal workpieces are joined together by a weld bead deposited by a manual or automatic welding torch head.

For some applications, the weld bead must be deposited in a narrow deep groove provided between the two workpieces to be joined together.

This is for example the case with steam generators for the loops of the primary cooling system of nuclear reactors when it is necessary to assemble, on site, two replacement steam generator parts during operations to replace worn-out steam generators.

These replacement steam generators comprise an outer casing formed from two parts, an upper part and a lower part, the upper part being attached to the lower part.

The upper part of the casing is joined to the lower part by butt welding these two cylindrical tubular parts of very large diameter, the facing joint surfaces of which are approximately horizontal.

These two workpieces provide between them, in their joint plan, a deep narrow welding groove that is directed horizontally.

The welding may be carried out manually or automatically by depositing successive layers of filler metal over the width of the groove until said groove has been completely filled.

During deposition of the various successive layers of the filler metal in the groove, it may happen that, for various reasons, the welding torch is improperly positioned and the welding filler metal may be incorrectly distributed, thereby resulting in protuberances or cave-ins of the weld bead.

To remedy this kind of defect and to prevent weld beads from failing to meet the technical specifications, successive layers of the weld bead are monitored.

However, one of the main difficulties to be overcome lies in the high temperature inside the groove, which is around 200° C.

Because of this constraint, and in certain cases owing to the narrowness of the groove, the use of illumination means and image acquisition means can be envisaged only by positioning them outside the groove.

This is for example the case with the use, as means for illuminating the bottom of the groove, of a point or plane laser beam emitted outside the groove approximately perpendicular to this groove.

In this case, the bottom of the groove is poorly illuminated, precluding an operator from correctly interpreting and analysing the images transmitted by the image acquisition means and, consequently, preventing him from being able to detect for example an undercut-type defect or a possible local cave-in of the weld beam.

The object of the invention is to provide a method and a device to make it possible, by means that are simple to implement, for the profile of a weld bead inside a groove provided between two metal workpieces to be displayed and monitored in a precise manner.

One subject of the invention is therefore a method of displaying and monitoring the profile of a weld bead inside a groove provided between two metal workpieces, characterized in that:

an assembly is placed inside the groove, said assembly comprising, facing one another, an image acquisition means, a light source, the beam of which is directed towards said image acquisition means, and, between the image acquisition means and the light source, a mask;

the optical axis of the image acquisition means is oriented so as to be approximately parallel to the sidewalls of the groove;

a light beam produced by the light source is directed towards the mask and the image acquisition means;

a central shadow zone and a peripheral halo are formed by means of the light beam and the mask, said halo illuminating, approximately perpendicularly, the weld bead and the sidewalls;

the profile of the weld bead and the sidewalls are displayed on a display/monitoring means; and said assembly is moved inside the groove longitudinally and parallel to the sidewalls.

According to other features of the invention:

said assembly is placed as close as possible to the weld bead;

the assembly comprising the image acquisition means, the light source and the mask is associated with a welding torch head and said assembly and the welding torch head are moved simultaneously inside the groove, longitudinally and parallel to the sidewalls, the welding torch head depositing the weld bead inside the groove;

the profile of the weld bead is monitored after it has solidified;

the profile of the weld bead is monitored during its formation and its solidification and, depending on predefined welding parameters, the welding torch head adjustment parameters are if necessary corrected;

before said assembly is placed inside the groove, the image acquisition means, the light source and the mask are arranged coaxially;

the distance between the light source and the mask is adjusted so as to optimize the halo illuminating the weld bead and the sidewalls;

the profile of the weld bead and the sidewalls are remotely displayed on a monitoring screen;

the dimensions of any defect in the weld bead are determined by comparing, directly on the monitoring screen or after image processing, the profile of the defect with the dimensions of the mask; and the images of the profile of the weld bead are recorded on an appropriate storage medium.

Another subject of the invention is a device for displaying and monitoring a weld bead deposited inside a groove provided between two metal workpieces, characterized in that it comprises:

inside the groove, an assembly comprising, facing one another, an image acquisition means, a light source, the beam of which is directed towards said image acquisition means, and, between the image acquisition means and the light source, a mask for forming a central shadow zone and a peripheral halo, said halo illuminating approximately perpendicularly the weld bead and the sidewalls; and outside the groove, display means for remotely displaying the profile of the weld bead and the sidewalls.

According to other features of the invention:

the assembly is linked to a manual or automatic welding torch;

the assembly is positioned downstream of the welding torch relative to its direction of movement in the groove at a distance of less than 100 cm;

the image acquisition means is formed by a camera;

the camera incorporates a microprocessor for analysing the images received according to predetermined welding parameters;

after the received images have been analysed in relation to predetermined welding parameters, the microprocessor produces signals for correcting the welding parameters of the automatic welding torch;

an endoscope is interposed between the mask and the camera; and the device includes means for producing warning signals intended to indicate a drift in the parameters of the weld bead to an operator so as to make a correction to the welding parameters.

Other features and advantages of the invention will become apparent on reading the following description given by way of example and with reference to the appended drawings, in which.

Figure 1:
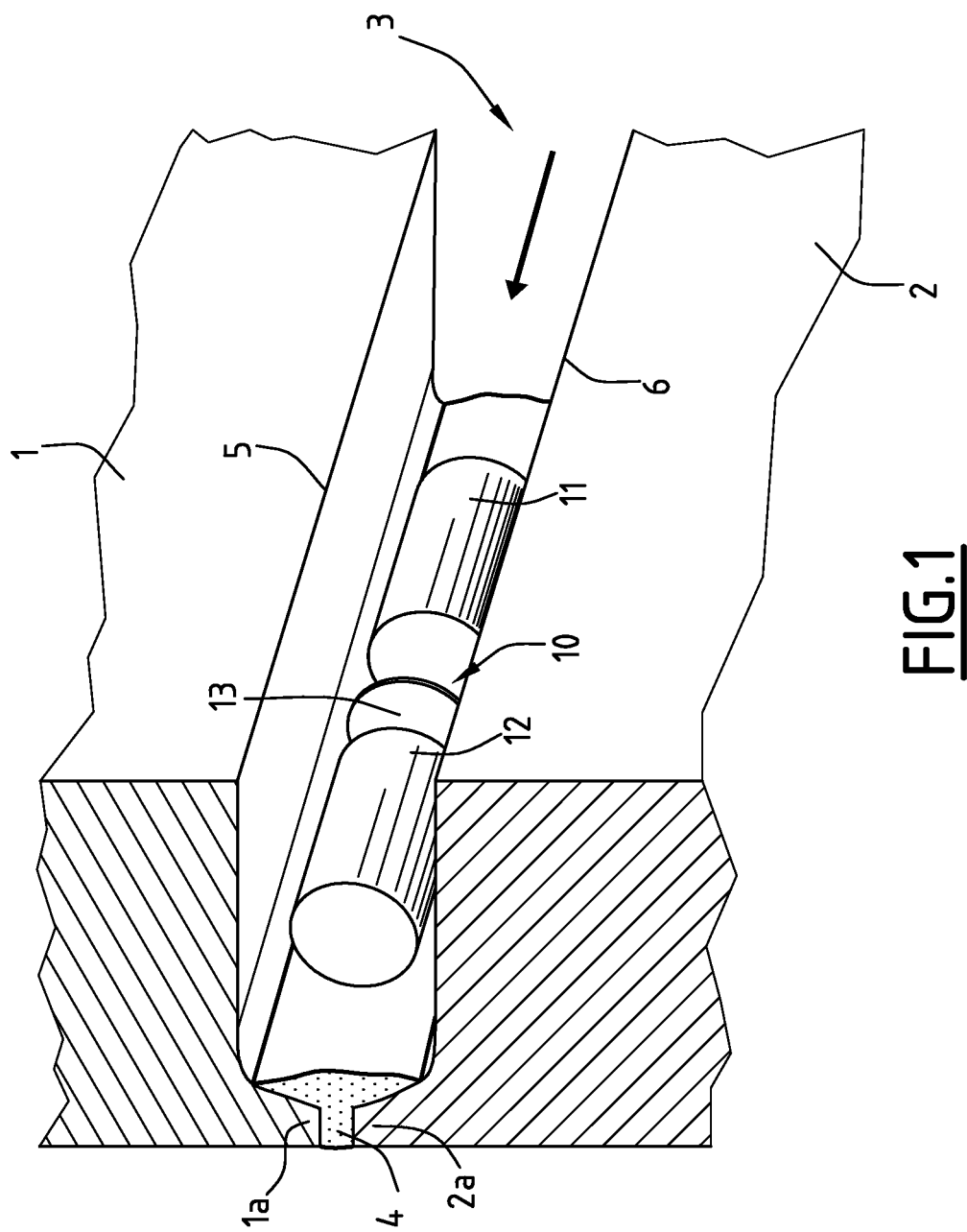
FIG. 1 is a schematic perspective view of a groove between two workpieces to be welded, placed in which groove is a device for displaying and monitoring the profile of a weld bead deposited therein.

FIG. 1 shows schematically, and in part, two workpieces 1 and 2 to be joined together, these having facing joint surfaces that define between them a welding groove 3 of precise and constant shape, along the entire length or the entire periphery of the workpieces 1 and 2, in which a weld bead 4 is produced.

To give an example, the workpieces 1 and 2 are produced so as to bear one on the other by support stubs, respectively 1a and 2a, and the groove 3 may be a narrow groove in which the sidewalls 5 and 6 of the workpieces 1 and 2 are approximately parallel or make a very small angle between them, for example an angle of less than 5°, or a broad groove, the faces of which make an angle of between 5° and 90°.

Depending on the application, the workpieces 1 and 2 may be welded by horizontal (flat position) welding or horizontal-vertical position welding or else vertical position welding using a manual or automatic welding torch head (not shown).

In addition, the welding may be linear or orbital welding.

Figure 2:
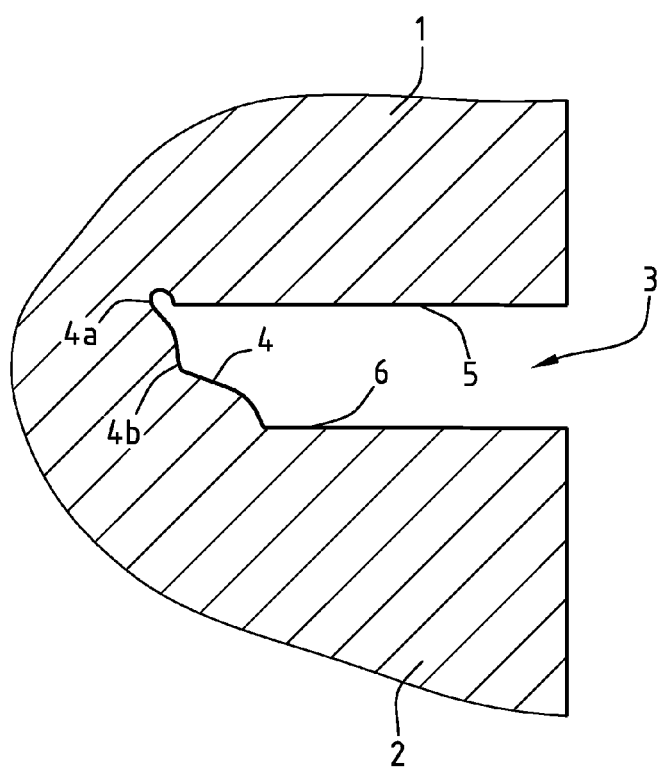
FIG. 2 is a schematic cross-sectional view of a weld bead with examples of defects.

During the deposition of the successive layers of the filler metal in the groove 3, there may occur, for various causes, as for example shown in FIG. 2, an undercut defect 4a on the sidewall 5 or 6 or a cave-in 4b of the weld bead, or a poor distribution of the filler metal.

To correct defects of this kind and to prevent weld beads from failing to meet the technical specifications, successive layers of the weld bead 4 are monitored by means of a device for displaying and monitoring the profile of this weld bead 4.

This display/monitoring device comprises an assembly denoted by the general reference 10.

The assembly 10 is placed inside the groove 3 and moved, either manually or automatically, simultaneously with the movement of a welding torch head, as will be seen later, to display the profile of the weld bead 4 and the sidewalls 5 and 6 of the groove 3.

In general, and as shown schematically in FIG. 1, the assembly 10 comprises three elements placed facing one another, respectively an image acquisition means 11, a light source 12 and a mask 13, the mask being placed between the image acquisition means 11 and the light source 12.

The beam of the light source 12 is directed towards the image acquisition means 11 and the optical axis of this image acquisition means 11 is oriented so as to be approximately parallel to the sidewalls 5 and 6 of the groove 3.

Conventionally, the light source 12 is linked via a cable to a power supply (not shown) and is formed for example by an incandescent lamp, by a light-emitting diode or by a flat laser, whether in a visible or non-visible spectrum, or by any other suitable member of a known type.

The assembly 10, formed by the image acquisition means 11, the light source 12 and the mask 13, is carried by a support 20 formed by a plate 21 (FIGS. 3 and 4), the thickness of which is defined so as to allow it to be positioned inside the groove 3.

Figure 3:
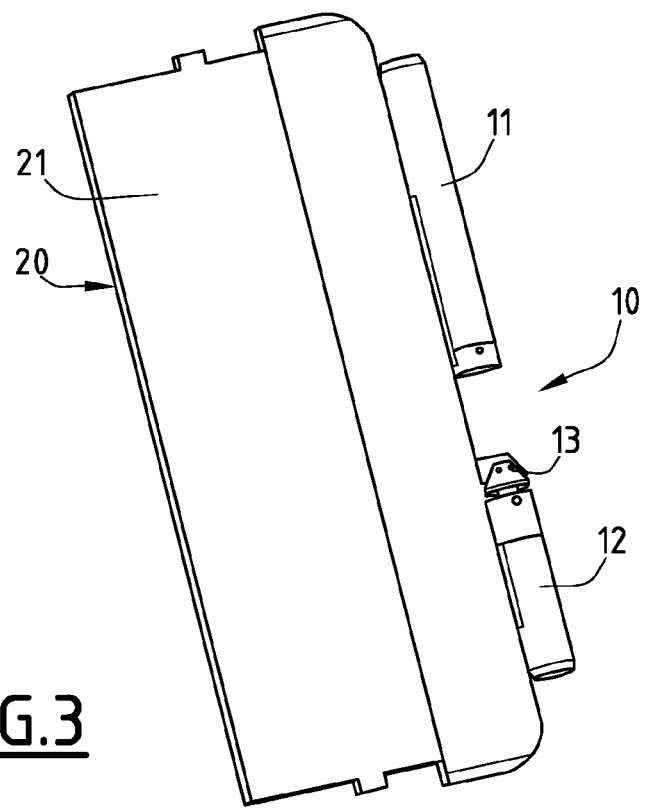
FIG. 3 is a schematic perspective view of a first embodiment of the display/monitoring device according to the invention.
Figure 4:
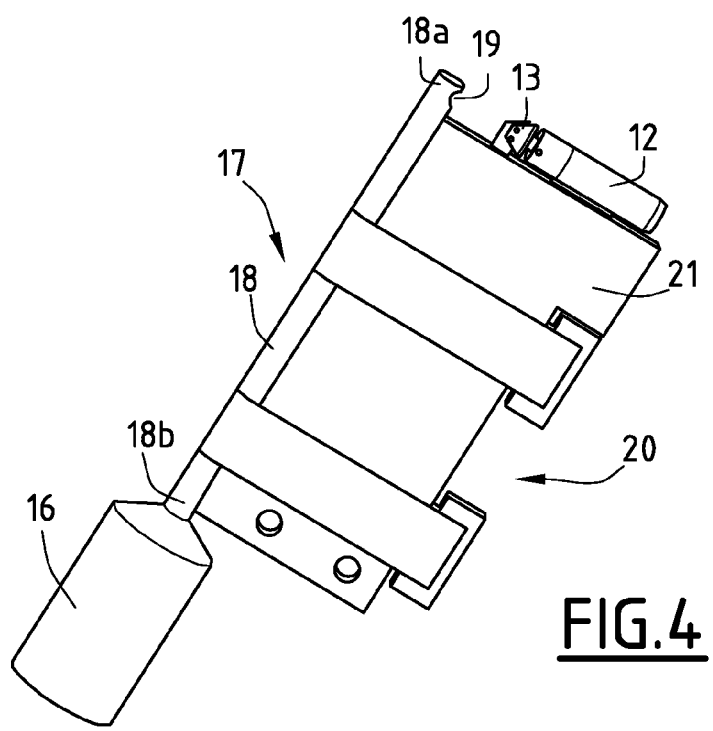
FIG. 4 is a schematic perspective view of a second embodiment of the display/monitoring device according to the invention.

As shown in FIGS. 3 and 4, the mask 13 preferably has the shape of a truncated cone, but other shapes may be envisaged such as, for example, the shape of a complete cone or the shape of a thin disc.

In the case of a mask 13 having the shape of a truncated cone or a complete cone, its base is placed opposite the light source 12.

This light source 12 is located as close as possible to the facing face of the mask so as to produce, in the direction of the mask 13 and the image acquisition means 11, a light beam, the resulting flux of which is directed towards the weld beam 4 and the sidewalls 5 and 6.

According to a first embodiment shown in FIG. 3, the image acquisition means is formed by a camera 11 carried by the plate 21 of the support 20 and positioned coaxially with respect to the light source 12 and to the mask 13.

With this embodiment, the assembly consisting of the camera 11, the light source 12 and the mask 13, carried by the plate 21 of the support 20, is positioned inside the groove 3 so as to monitor the profile of the weld bead 4 and the sidewalls 5 and 6 of this groove 3.

According to a second embodiment, shown in FIG. 4, the light source 12 and the mask 13 are positioned coaxially and the image acquisition means consists of a camera 16 positioned so as to be perpendicular to said light source 12.

In this embodiment, an intermediate element for conveying the image is positioned between the light source 12 and the camera 16. This intermediate element consists for example of a means of the endoscope type 17, comprising a tube 18, a first end 18a of which is provided with a window 19 positioned on the axis of the light source 12 and a second end 18b of which is connected to the camera 16. The tube 18 of the endoscope 17 contains the necessary optical components of known type, such as for example prisms or mirrors, allowing the image to be oriented and conveyed as far as the camera 16. This endoscope 17 contains no light source.

With the embodiment shown in FIG. 4, when the profile of the weld bead 4 and the sidewalls 5 and 6 are being monitored, only the light source 12, the mask 13 and the end 18a of the tube 18 of the endoscope 17 are positioned inside the groove 3 close to the weld bead 4.

The camera 11 or 16 is linked via a cable to a means of displaying and monitoring the images, which preferably consists of a screen (not shown) for remotely displaying the profile of the weld bead 4 and the sidewalls 5 and 6.

The profile of the weld bead 4 and the sidewalls 5 and 6 of the groove 3 are monitored in the following manner.

Before the profile of the weld bead 4 is monitored, the camera 11, the light source 12 and the mask 13 are positioned coaxially on the plate 21 of the support 20 in the case of the embodiment shown in FIG. 3 or the end 18a of the tube 18 of the endoscope 17, the light source 12 and the mask 13 are positioned coaxially on the plate 21 of the support 20 in the case of the embodiment shown in FIG. 4.

Next, the assembly 10 is placed in the groove 3, the optical axis of the camera 11 or the optical axis of the window 19 of the endoscope 17 is oriented so as to be parallel to the sidewalls 5 and 6 of the groove 3, and the distance between the light source 12 and the mask 13 is adjusted so as to optimize the illumination of the weld bead 4 and the sidewalls 5 and 6.

Figure 5:
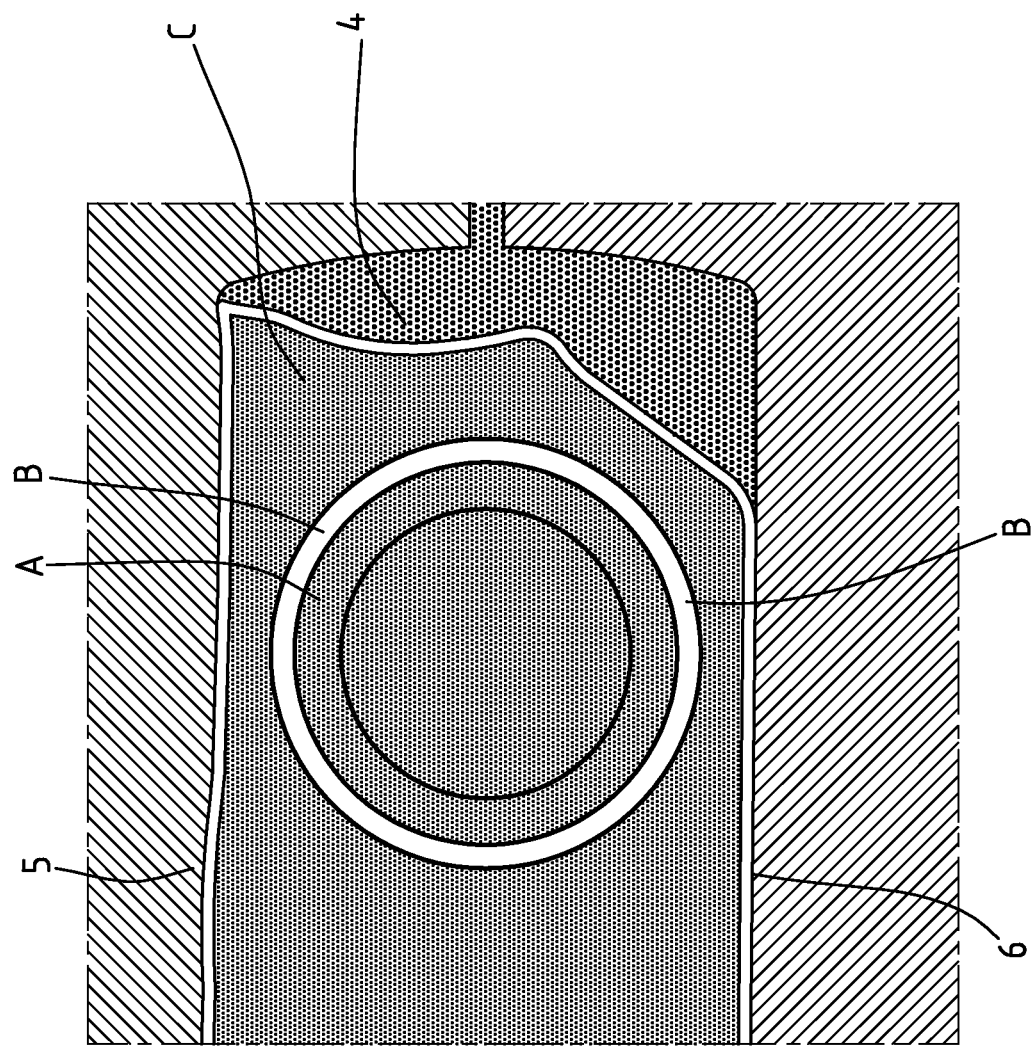
FIG. 5 is a representation of an image of the profile of the weld bead, said image being produced by means of the display/monitoring device according to the invention.

FIG. 5 shows the image obtained on a display/monitoring screen when the assembly 10 is positioned in the groove 3 and moved parallel to the weld bead 4.

The light source 12 produces, in the direction of the mask 13, a light beam that has the effect, as shown in FIG. 5, of forming a central shadow zone A corresponding to that part of the light source 12 which is concealed by the mask 13, and a peripheral halo B corresponding to that part of the light source 12 which is visible by the camera around the mask 13, said peripheral halo B illuminating, approximately perpendicularly, the weld bead 4 and the sidewalls 5 and 6 of the groove 3.

In FIG. 5, the dark zone C, lying between the halo B on the one hand and that portion of the profile 4 illuminated and flanked by the portions of the illuminated sidewalls 5 and 6 on the other, corresponds to the surfaces of the weld bead 4 and to the surfaces of the walls 5 and 6 that are not illuminated, forming the background of the light source 12.

The assembly 10 is moved inside the groove 3 longitudinally and parallel to the walls 5 and 6, thereby making it possible to display and monitor the profile of the weld bead 4 and the sidewalls 5 and 6.

This monitoring may be accomplished after the weld bead 4 has solidified or during its formation and its solidification, thus making it possible to correct, if necessary, the welding torch head, parameters adjustment according to predefined dimensional or qualitative weld bead criteria.

By displaying the profile of the weld bead 4 it is possible to determine the dimensions of any defect in this weld bead 4 by directly comparing, on the monitoring screen, the profile of the defect with the dimensions of the mask 13.

The images of the profile of the weld bead 4 may be recorded.

As shown in FIG. 5, the contrast thus obtained between the shadow zone and the zones illuminated by the luminous halo makes it possible for an operator viewing the images on the monitoring screen to immediately detect a weld bead defect.

The assembly 10 is combined inside the groove 3 with a manual welding torch or with an automatic welding torch.

A description will now be given, with reference to FIGS. 6 and 7, of an example of the use of the assembly 10 with an automatic welding torch head for the narrow-groove/horizontal-vertical position welding of two large-diameter tubular cylindrical workpieces of a nuclear reactor component, such as for example a steam generator.

Figure 6:
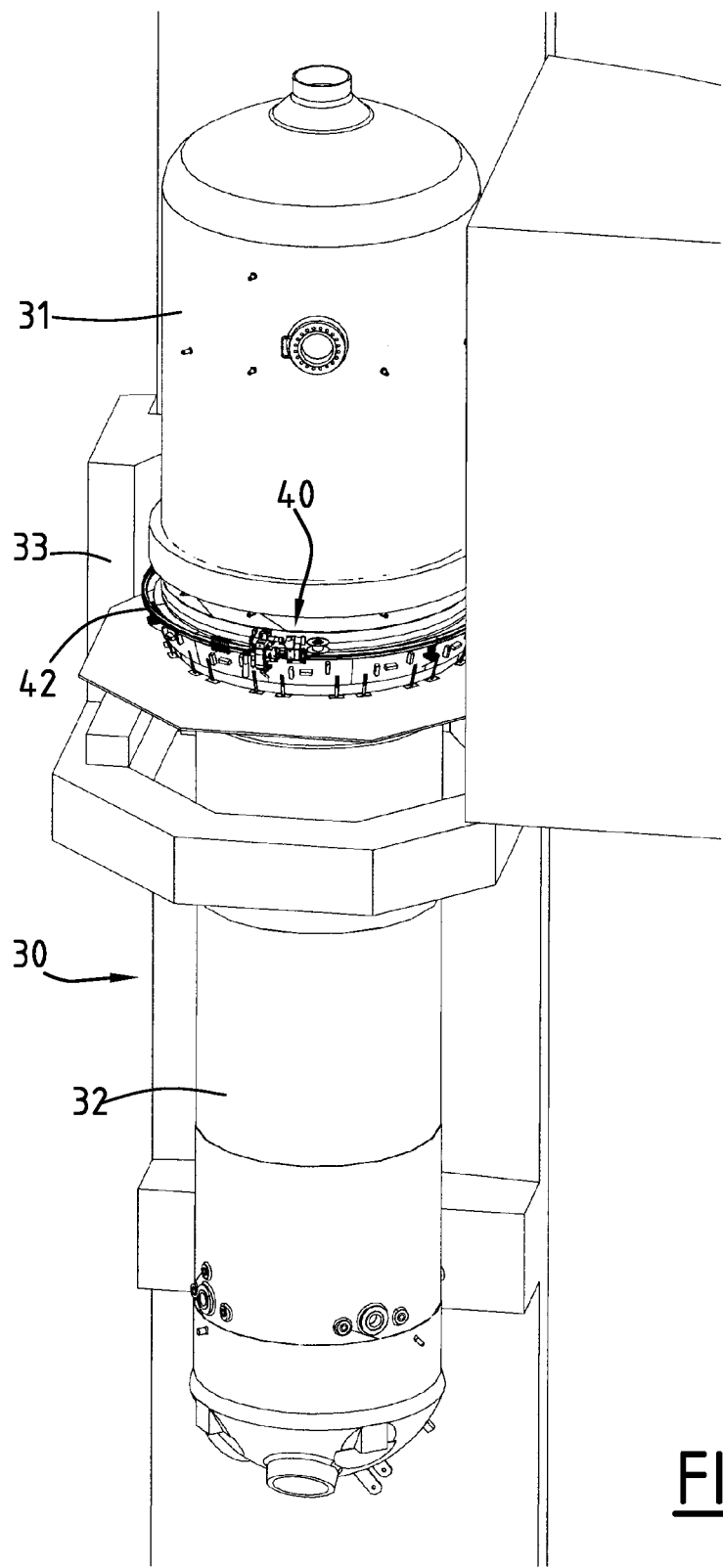
FIG. 6 is a schematic perspective view of a steam generator and of an automatic welding device equipped with the display/monitoring device according to the invention.

FIG. 6 shows a steam generator 30, the outer casing of which is conventionally made up of two parts, 31 and 32 respectively, which are introduced separately into a casemate 33, the upper part 31 of the steam generator 30 being attached to the lower part 32, which was put into position and connected beforehand to the primary cooling system of the reactor.

To make the join, the two workpieces 31 and 32 to be joined are placed end to end so as to have facing joint surfaces which are carefully machined so as to define between them a welding groove (not shown) of precise and constant shape, over the entire periphery of the workpieces 31 and 32, along which a weld bead is produced.

To give an example, the groove has a depth of around 90 mm and a width of around 10 mm.

To produce the weld bead between the workpieces 31 and 32 placed in a superposed assembly arrangement, usually denoted by the expression "horizontal-vertical position", requires the use of a suitable welding device and movement/control means for carrying out welding operations completely automatically by remote control, while ensuring perfect quality of the weld.

Such an automatic welding device denoted in its entirety by the reference 40 in FIG. 6 has been described in French Patent Application 2 877 246.

In the present case, the automatic welding device 40 is combined with a device for displaying and monitoring the profile of the weld bead deposited in the groove provided between the two workpieces 31 and 32.

Figure 7:
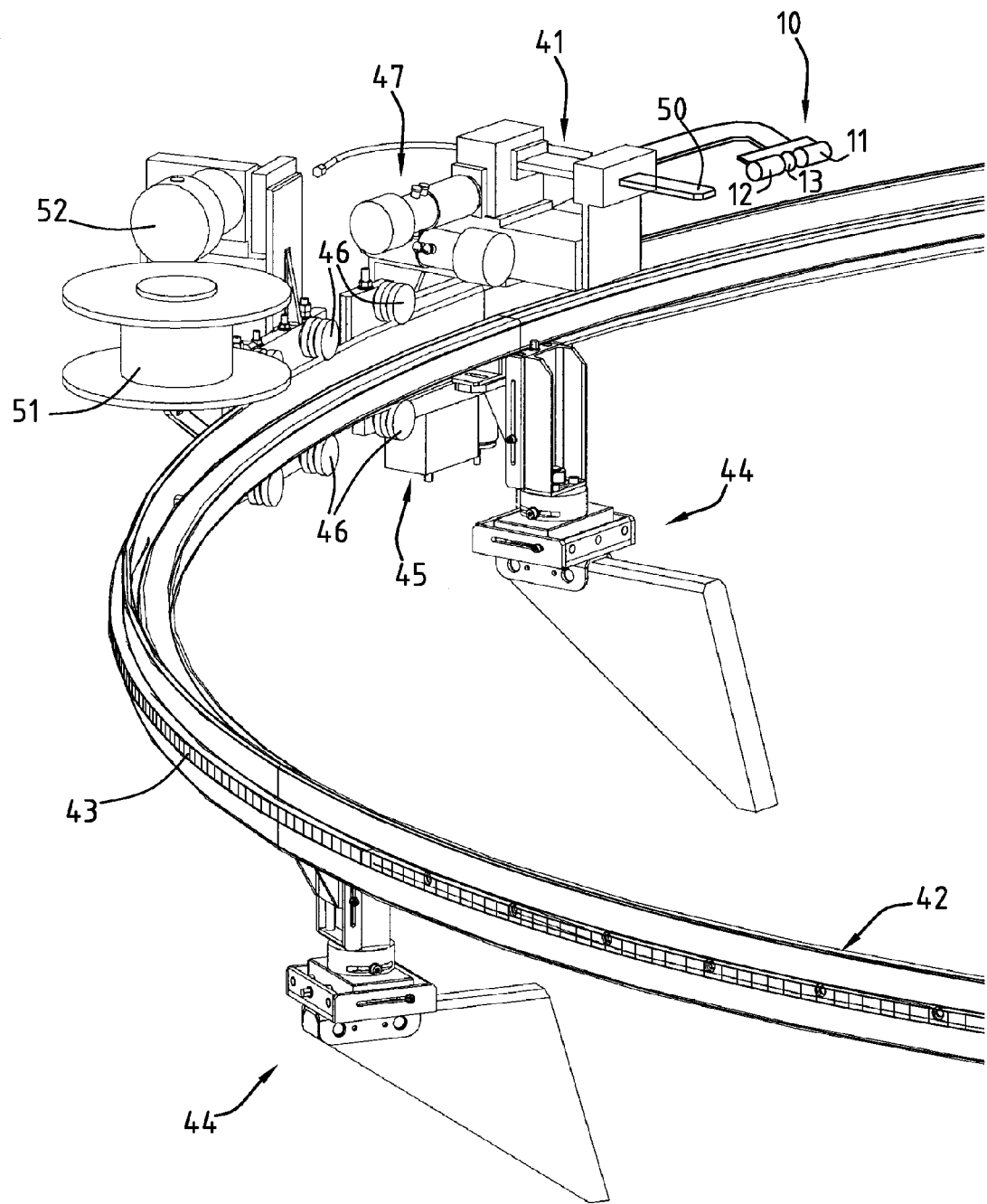
FIG. 7 is a schematic view on a larger scale of the automatic welding device equipped with the display/monitoring device according to the invention.

As shown in FIG. 7, the automatic welding device denoted by the general reference 40 is made up in particular of a welding head 41 and a rail 42 on which this welding head 41 runs. This rail 42 is concentric with the workpiece 31 and has, on its external face opposite that facing the workpiece 31, a rack 43.

This rail 42 made up of several juxtaposed sections linked together by suitable means of conventional type (not shown) is fastened to the workpiece 31 by uniformly distributed feet 44.

The welding head 41 is moved on the rail 42 around the workpieces 31 and 32 by a carriage 45 carrying in particular the welding head 41 and equipped with rollers 46 on the upper edge and the lower edge of the rail 42 respectively. The carriage 45 is moved by an electric motor (not shown) carried by this carriage 45, the output shaft of which motor rotates a pinion (not shown) which meshes with the rack 43 of the rail 42.

The assembly for supporting the welding torch 41 includes means 47 for moving this welding torch 41 in the depth direction of the groove and also for moving it in the width direction of this groove.

The head of the welding torch 41 has a front part 50 intended to be introduced into the groove between the workpieces 31 and 32 and this head has a thickness substantially smaller than the width of this groove.

The welding torch 41 is conventionally fed with a filler metal wire (not shown) through which an electric current passes so as to melt the wire inside the groove by an electric arc.

The filler metal wire is wound on a storage reel 51 and a motorized device 52 allows the welding torch 41 to be fed with filler metal wire.

As shown in FIG. 7, the head of the welding torch 41 is combined with an assembly 10 for displaying and monitoring the profile of the weld bead inside the groove provided between the workpieces 31 and 32. This assembly 10 is identical to one of the above embodiments and comprises a light source 12, a mask 13 and either a camera 11 (FIG. 3) or a camera 16 combined with an endoscope 17 (FIG. 4).

This assembly 10 is positioned downstream of the welding torch 41 relative to its direction of movement in the groove at a distance of less than 100 cm therefrom.

Thus, during formation of the weld bead inside the groove by the head of the welding torch 41, the assembly 10 makes it possible to display and monitor the profile of the weld bead and the sidewalls of the groove provided between the workpieces 31 and 32.

This monitoring of the weld bead profile is carried out during formation and solidification of said weld bead and, depending on predefined welding parameters, the parameters for adjusting the head of the welding torch 41 may be corrected.

To do this, the camera 11 or 16 may incorporate a computer or microprocessor allowing the received images to be analysed according to predetermined welding parameters.

According to a variant, the computer or microprocessor may be independent of the camera 11 or 16.

After the received images have been analysed relative to the predetermined welding parameters, the microprocessor, incorporated into the camera or not, may produce signals for correcting the welding parameters of the automatic welding torch.

In general, with the display/monitoring device according to the invention combined with a welding torch head, two types of corrections to a weld bead may be envisaged.

If a defect is identified on the image obtained by the camera or analysed directly by this camera, it is possible, according to certain criteria, to warn an operator, who stops the welding and takes the corrective actions.

If the defect is considered to be an unimportant defect, the operator may decide to continue depositing the weld bead so that, during the second pass, on the next turn, this defect will advantageously be melted without the need to stop and make a local repair to the weld bead.

In the case of automatic welding, it is possible to send commands for correcting the welding parameters to the welding torch so as to avoid accentuating a drift towards poor quality of the weld bead, which would then become non-conforming.

The detection of any slipping of certain welding parameters towards unacceptable values may be analysed either by a controller, who is monitoring the process on a monitoring screen on which he sees the view taken by the camera and visual means superposed on the image allowing him to assess the drift in shape of the weld bead, or by the computer that may or may not be incorporated into the camera, according to the variations in certain parameters chosen beforehand.

The invention claimed is:

1. A method of displaying and monitoring a profile of a weld bead inside a groove provided between two metal workpieces, wherein:

an assembly is placed inside the groove, said assembly comprising, facing one another, an image acquisition means, a light source, a beam of which is directed towards said image acquisition means, and, between the image acquisition means and the light source, a mask;

the optical axis of the image acquisition means is oriented so as to be approximately parallel to the sidewalls of the groove;

a light beam produced by the light source is directed towards the mask and the image acquisition means;

a central shadow zone and a peripheral halo are formed by means of the light beam and the mask, said halo illuminating, approximately perpendicularly, the weld bead and the sidewalls;

the profile of the weld bead and the sidewalls are displayed on a display/monitoring means; and said assembly is moved inside the groove longitudinally and parallel to the sidewalls.

2. The method according to claim 1, wherein said assembly is placed as close as possible to the weld bead.

3. The method according to claim 1, wherein:

the assembly comprising the image acquisition means, the light source and the mask is associated with a welding torch head; and said assembly and the welding torch head are moved simultaneously inside the groove, longitudinally and parallel to the sidewalls, said welding torch head depositing the weld bead inside the groove.

4. The method according to claim 1, wherein the profile of the weld bead is monitored after the weld bead has solidified.

5. The method according to claim 1, wherein the profile of the weld bead is monitored during formation and solidification of the weld bead and, depending on predefined welding parameters, the welding torch head adjustment parameters are if necessary corrected.

6. The method according to claim 1, wherein, before said assembly is placed inside the groove, the image acquisition means, the light source and the mask are arranged coaxially.

7. The method according to claim 1, wherein the distance between the light source and the mask is adjusted so as to optimize the halo illuminating the weld bead and the sidewalls.

8. The method according to claim 1, wherein the profile of the weld bead and the sidewalls are remotely displayed on a monitoring screen.

9. The method according to claim 1, wherein the dimensions of any defect in the weld bead are determined by comparing, directly on the monitoring screen or after digital image processing, the profile of the defect with the dimensions of the mask.

10. The method according to claim 1, wherein the images of the profile of the weld bead are recorded.

11. A device for displaying and monitoring a profile of a weld bead deposited inside a groove provided between two metal workpieces, wherein the device comprises:

inside the groove, an assembly comprising, facing one another, an image acquisition means, a light source, a beam of which is directed towards said image acquisition means, and, between the image acquisition means and the light source, a mask configured to form a central shadow zone and a peripheral halo, the mask being further configured to direct light from said halo approximately perpendicular toward the weld bead and the sidewalls; and outside the groove, display means for remotely displaying the profile of the weld bead and the sidewalls.

12. The device according to claim 11, wherein the assembly is linked to a manual welding torch.

13. The device according to claim 11, wherein the assembly is linked to an automatic welding torch.

14. The device according to claim 12, wherein the assembly is positioned downstream of the welding torch relative to a direction of movement in the groove at a distance of less than 100 cm.

15. The device according to claim 11, wherein the image acquisition means is formed by a camera.

16. The device according to claim 15, wherein the camera incorporates a microprocessor for analysing the images received according to predetermined welding parameters.

17. The device according to claim 16, wherein, after the received images have been analyzed in relation to predetermined welding parameters, the microprocessor produces signals for correcting the welding parameters of an automatic welding torch.

18. The device according to claim 11, wherein an endoscope is interposed between the mask and the camera.

19. The device according to claim 11, including means for producing warning signals intended to indicate a drift in the parameters of the weld bead to an operator so as to make a correction to the welding parameters.

* * * * *